United States Patent [19]

Ernst

[11] 4,023,401

[45] May 17, 1977

[54] HAND-OPERABLE DUROMETER

[76] Inventor: Alfred Ernst, Casa Carolina, Curio Ticino, Switzerland

[22] Filed: Mar. 8, 1976

[21] Appl. No.: 664,471

[30] Foreign Application Priority Data

Mar. 12, 1975 Switzerland .................... 3141/75
Apr. 10, 1975 Switzerland .................... 4596/75

[52] U.S. Cl. .................................................. 73/81
[51] Int. Cl.² ........................................ G01N 3/42
[58] Field of Search ............... 73/81, 85, 78, 84, 80

[56] References Cited

UNITED STATES PATENTS

| | | | |
|---|---|---|---|
| 2,667,066 | 1/1954 | Ernst | 73/81 |
| 2,667,067 | 1/1954 | Pocknee | 73/81 |
| 3,200,640 | 8/1965 | Ernst | 73/81 |

*Primary Examiner*—James J. Gill
*Assistant Examiner*—Anthony V. Ciarlante
*Attorney, Agent, or Firm*—Michael J. Striker

[57] ABSTRACT

A hand-operable durometer has a connection allowing a limited universal pivoting movement between an outer casing and an inner shell in order to facilitate the manual application of a truly axial thrust to a penetrator tip disposed largely within the shell.

18 Claims, 11 Drawing Figures

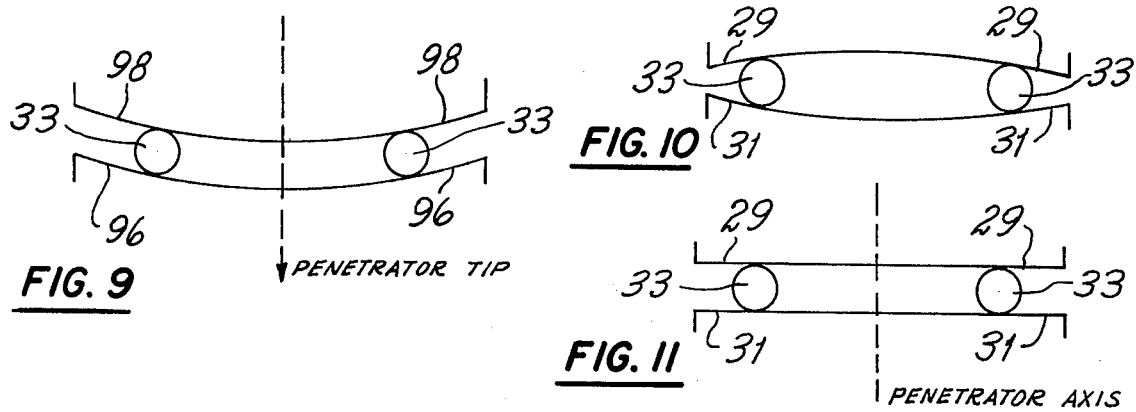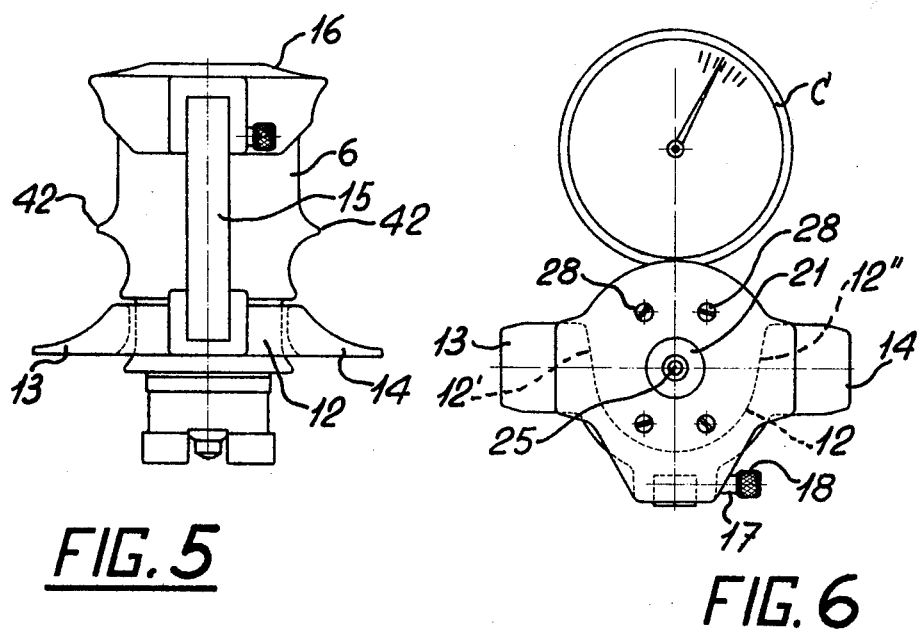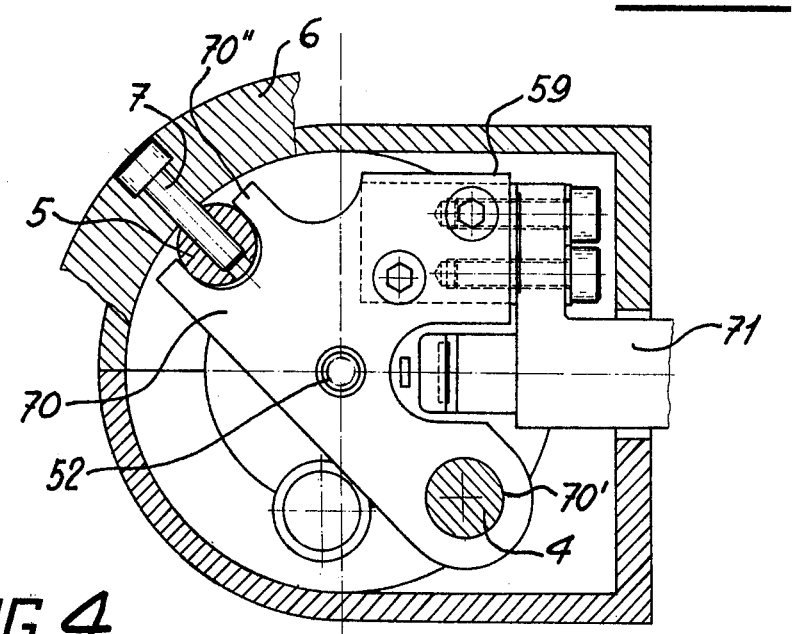

HAND-OPERABLE DUROMETER

FIELD OF THE INVENTION

The present invention relates to a hand-operable durometer, which is pressed by hands against the surface to be tested. It may be so pressed by the use of two diametrally opposed and laterally projecting abutments. The hardness is read on a comparator included in the durometer.

BACKGROUND OF THE INVENTION

Portable durometers are known, in which the measurement is effected exerting a thrust with the hands on adzuate projections projecting from the housing of the instrument. Said housing must transmit to the inside member of the instrument a thrust as coaxial as possible relative to the penetrator, in order to avoid wrong measurements.

It happens however that the thrust exerted with the hands is not always perfectly coaxial with the instrument and this is due to various factors, only some of which can be dependent on the operator's attention. The most frequent reason for such an eccentricity of the thrust is due to an untrue abutment of the hands on suitable projections.

Other reasons are the surface inclination of the piece to be measured and the necessity to effect measurements with the apparatus obliquely positioned or horizontally directed. Usually, the operator finds it difficult to realize that the thrust exerted by him is not axial and therefore he cannot readily determine whether the taken measurement is right or not.

The basic aim of the present invention is to avoid or reduce this eccentricity. With the durometer disclosed and illustrated herein, it is possible to apply the thrust easily according to a substantially axial direction.

SUMMARY OF THE INVENTION

A durometer according to the invention comprises an outer structure, on which the pressure, oscillating, or movable, is exerted with respect to the instrument axis, in order to be moved by hands in the right position to transmit to the instrument a substantially axial thrust.

Acciording to a further feature of this invention, reference means is provided to survey an abnormal position of said oscillating structure, in order to permit the operator to carry it back in a correct measurement position.

In order to allow a better employment of the durometer in determined positions in which it is not possible to exert the thrust through said abutments or on surfaces not easily accessible, according to a further feature, said diametrally opposed abutments are integral with a casing independent from the shell of the instrument and surrounding the latter, said casing being connected in a detachable way to an upper cover, while this comparator is disposed laterally to the instrument and outside the plan encumbrance of this instrument.

In this way the instrument can be advantageously employed in three ways. According to a first way, the thrust can be exerted through the lateral abutments and the measurement can be read on the comparator. In the second way, the abutments can be eliminated disassembling the elements which are connected to the upper cover, and exerting the thrust on the same cover. The user can read the measurement on the comparator. The thrust on the cover can be exerted with one hand retaining the apparatus, and the other hand applied on its outer cover, in order to secure the bearing on the surface to be measured, or with both the hands. In a third way, in particularly difficult measurement positions, it is possible to employ the instrument with two operators, one of whom keeps the instrument stable on the surface to be measured and the other presses with the hands on the cover.

BRIEF DESCRIPTION OF THE DRAWINGS

Two preferred particular embodiments of the invention are shown, by way of example but not of limitation, in the enclosed drawings, in which:

FIG. 4 is a second plan view in cross-section according to the line IV—IV of FIG. 1;

FIG. 5 is an outer view of the durometer according to the previous figures, taken by the opposed side of the comparator;

FIG. 6 is a plan view of the durometer according to the previous figures;

FIG. 9 is a cross-section of part of a second embodiment of the durometer;

FIG. 10 is a cross-section of part of a first-embodiment of the durometer;

FIG. 11 is a cross-section of part of a first-embodiment of the durometer.

DESCRIPTION OF A PARTICULAR EMBODIMENT

Figure 1:
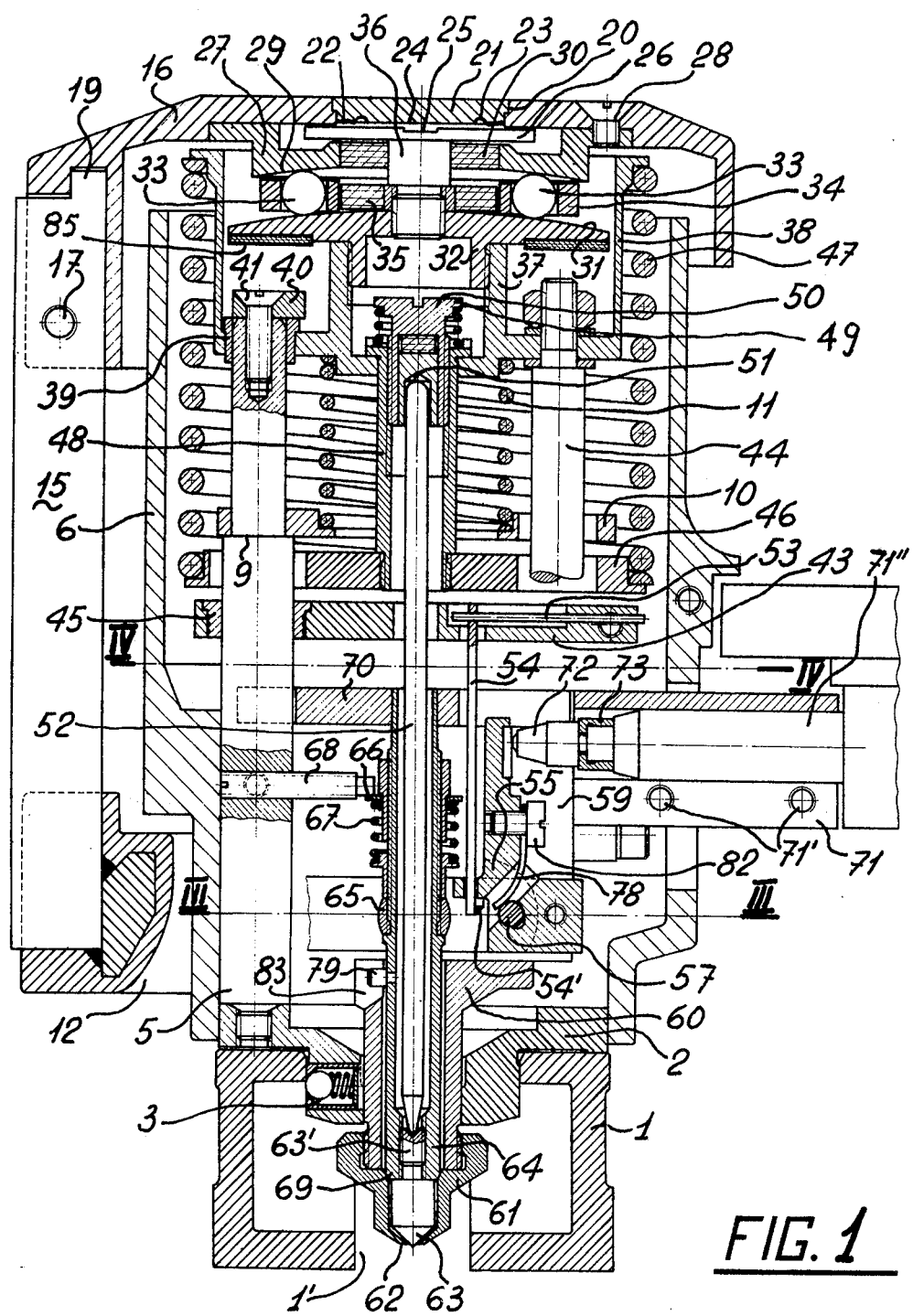
FIG. 1 is a cross-section of a first embodiment of the durometer according to the invention executed according to the line I — I of FIG. 3.
Figure 2:
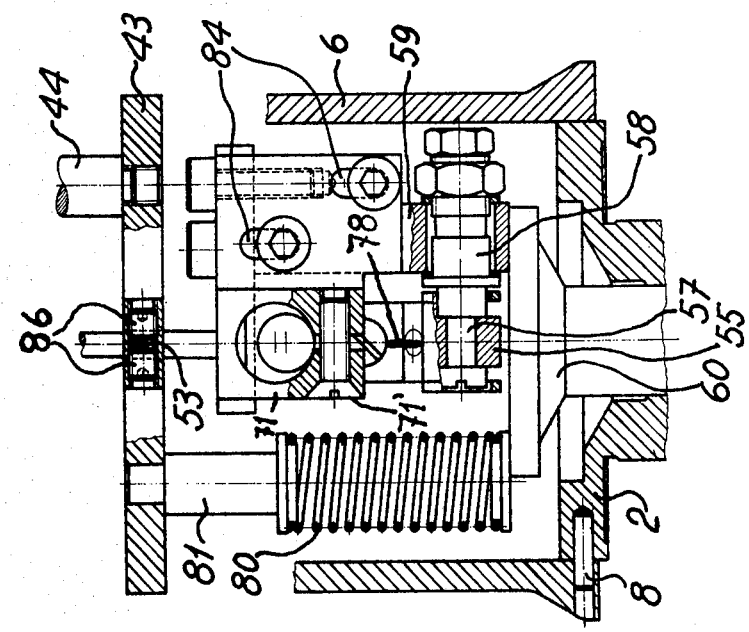
FIG. 2 is a cross-section executed according to a broken line II — II of FIG. 3.

Referring to FIGS. 1 to 6, the durometer according to a first embodiment of the invention includes a first assembly of fixedly connected members. The first assembly is fixed when the instrument is in a work position, and comprises a base 1 which bears on the surface to be measured and has a central opening 1' which permits the passage of a reference ring nut 61 and of the penetrator 63, as will be explained later. The first assembly also includes a flange 2 which supports by release connection, for example by a ball device, the base 1, two columns 4 and 5 (FIGS. 1 and 3) extending upwardly from the flange 2 and of which only the column 5 is visible in FIG. 1, and in addition a protective shell 6, composed by two connected half-shells, fixed to the column 5 by means of a screw 7 (FIG. 4) and to the flange 2 by means of a pin 8 (FIG. 2).

The columns 4 and 5 have towards their tops a sudden diameter reduction to form an annular shoulder against which abuts a disc 10. This has some holes for coupling with the two columns as well as some holes for the passage of other vertical members as will be explained.

The disc 10 serves as an abutment seat for a compression spring 11 whose other end acts against a second (movable) assembly of members. This movable assembly comprises a partial ring 12 having its plane perpendicular to the axis of the instrument and encircling the housing 6 at an adequate distance for more than 180°. The ring 12 has a flared opening of the ends 12' and 12'' (FIGS. 1 and 6) from which two handles or abutments 13 and 14 extend outwardly and in a diametrally opposed direction. These handles are able to receive a work thrust from the operator's hands.

From a median portion of the partial ring 12, a connecting member, such as a stout rod 15, extends upwardly. It is connected to the top end to an upper cover 16. The connection between the cover 16 and the rod 15 includes a screw 17, having a knurled head 18 and a lug and slot joint 19 which prevents the relative rotation between rod 15 and cover 16 on the screw 17. The rod 15, further, serves as a counterweight for the comparator which will be described below.

The cover 16 has a central through hole seat 20, in which a small disc 21 of transparent material is housed. This disc 21 has on its lower surface a visible circular peripheral ring 22, not transparent and preferably coloured. The ring 22 is internally rimmed by an annular groove 23 which delimits a central circular transparent area 24, which permits the user to see an underlying reference index, such as a circular depression 25, provided in a disc 26. This permits the operator to effect the truing of the thrust during the hardness measurement.

Figure 7:
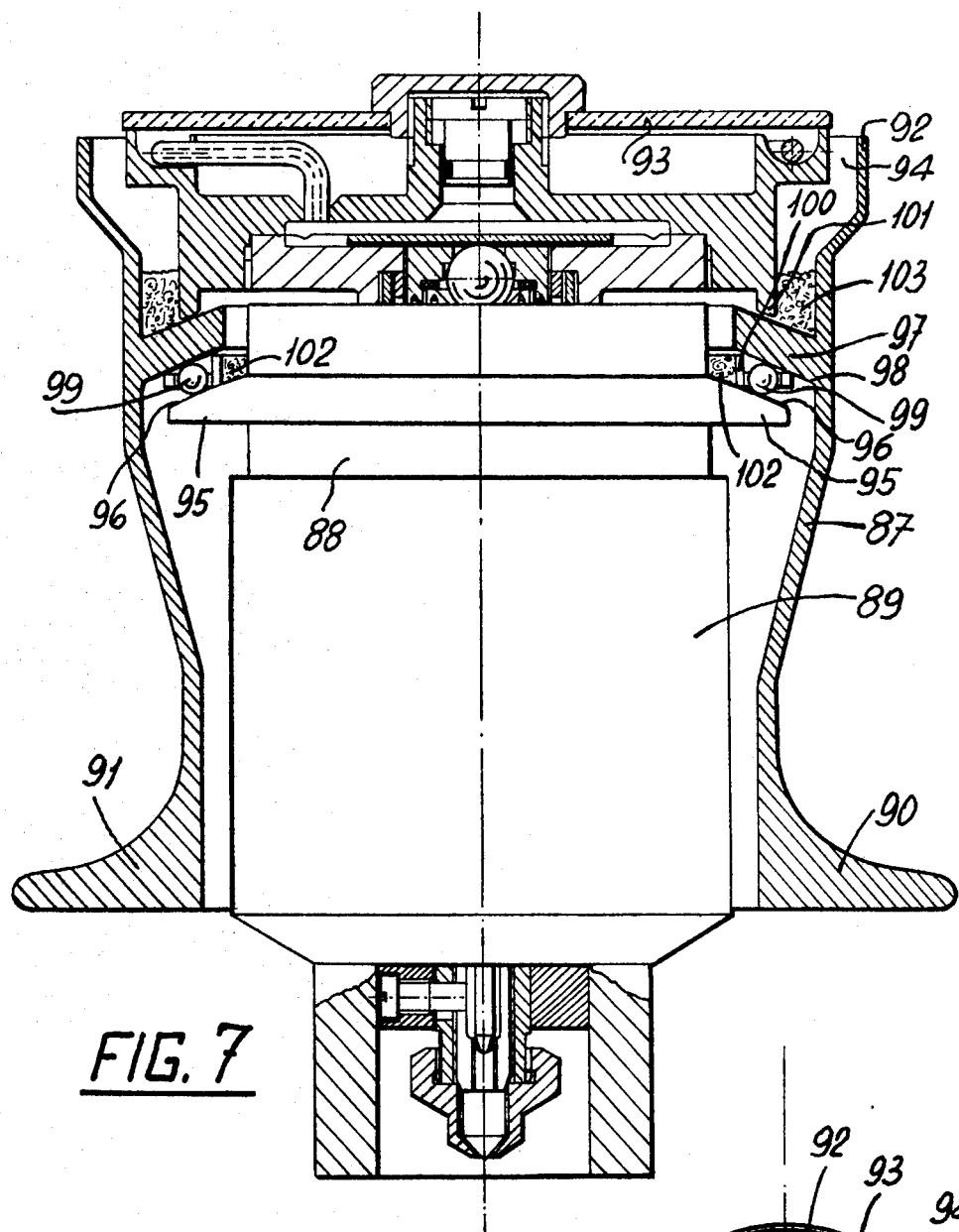
FIG. 7 is an axial section of the durometer according to the invention, in a second embodiment.

Below the cover 16, a flange 27 is fixed thereto by screws 28 (FIGS. 1 and 7). Said flange has a lower spherical surface 29 delimiting an axial hole in which a resilient ring 30 is clamped.

In confronting relationship with the spherical area 29 is prearranged a second spherical surface 31, supported by an externally threaded boss 32. Between the spherical surfaces 29 and 31 a ball row 33 is interposed supported by an annular cage 34, the latter being equipped internally with a second resilient ring 35 which is coaxial and faces the resilient ring 30.

From the spherical surface 31, a pin 36 extends axially upwards and is inserted through the center of the resilient rings 30 and 35. The pin 36, above the ring 30, supports the disc 26 carrying the reference index 25. The two spherical surfaces 29 and 31 have a common center arranged on the instrument axis, preferably near the abutting point of the penetrator tip on the surface to be measured. In this way, the cover 16 can oscillate with respect to the disc 26, so as to allow the operator to apply a true axial thrust. This can be determined by the central transparent area 24 coinciding with the reference index 25. The resilient rings 30 and 35 have the function to damp the relative movement between the cover 16 and the first assembly, and to return it towards the true axial position.

In some alternative embodiments, the common center of the spherical surfaces 29 and 31, even if it is placed on the instrument axis, it can be placed above the abutments 13 and 14, or directly above the same spherical surfaces which then of course will be concave upwardly. It is also possible that the surfaces 29 and 31 are planar. It is not an essential condition that the surfaces 29 and 31 are concentric; they can have different radii.

The boss 32 is screwed in the central bush 37 of a cup-shaped member 38 the base of which, in correspondence with the columns 4 and 5, has respective holes equipped with anti-friction bushes, one of which is shown at 39. At rest, the upward movement of the cup 37 under the action of spring 11 is stopped by a shoulder 40 secured at the end of the respective column by a screw 41.

A lower surface of the cup 38 forms the upper spring seat for the spring 11.

All the members above described from item 12 onwards constitute the second assembly of members which in use move together in a generally axial direction, under the thrust exerted by the operator. As can be seen from FIGS. 1, 5 and 6, the operator thrust can be exerted by the hands on the abutments 13 and 14. In the case of a particular measurement position, in which it is not comfortable for the operator to exert the thrust on said abutments, and even in the case in which the partial 12 can be an encumbrance for the same operator, the latter can exert the thrust acting directly on the cover 16, with one or both hands, and if it is necessary he can disassemble the rod 15 unscrewing the screw 17 and then removing with said screw also the partial ring 12. When the thrust exerted on the cover 16 is effected with a single hand, the instrument can be kept stable on the surface to be tested by holding the shell 6 with the other hand. The shell 6 for this purpose has some suitable projections 42 (FIG. 5) facilitating a sure holding. As previously indicated, if desired, a first operator can act on the cover and a second one can keep the instrument stable by holding the outside of shell 6.

The cup 38 is fixed to a lower plate 43, disposed at an adequate distance, by means of some spacers 44 (FIGS. 1 and 2), of which only one is visible; the columns 4 and 5 extend through the plate 43 and, at least around one of the columns there is a bush 45 of anti-friction material.

A spring 47 is arranged between the upper projecting edge of the cup 38 and a flange 46 placed a little above the plate 43. This spring 47 serves to supply the resilient bias against which the tip 63 is forced into the surface to be tested, said plate 43 being suitably bored for the passage of the columns 4 and 5 and the spacers 44.

The flange 46 has a central threaded hole in which the end of a tubular cylinder 48 is screwed, said end extending axially upwardly so as to enter slidingly an axial hole in the cup 38. The cylinder 48 above said hole has an annular shoulder 49, which constitutes a stop defining the maximum spacing between the flange 46 and the cup 38, under the action of the spring 47.

On the cylinder 48, a plug 50 is screwed, said plug having an axial seat 51 in which the upper end of a rod 52 is housed, said upper end transmitting the force to the penetrator, said plug 50 being adjustable to adjust the axial play of said rod 52.

Figure 3:
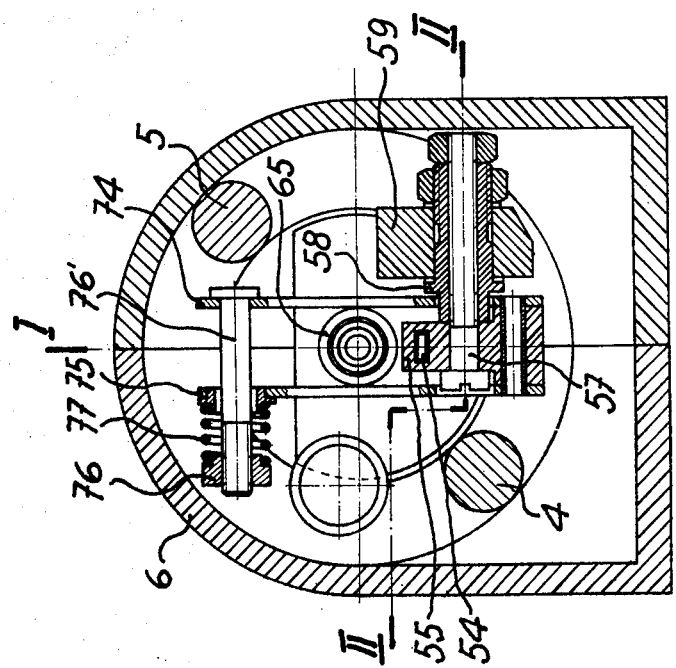
FIG. 3 is a plan view in cross-section according to a line III — III of FIG. 1.

A tie rod 54 is connected to the plate 43, by means of a bar 53. The tie rod 54 acts by means of an end hook 54' on a block 55. The block 55 is mounted for rotational movement about a pin 57. The latter is fixed through a sleeve 58 to a vertical rod 59 (FIGS. 1, 2 and 3). The rod 59 is secured to a sleeve stem 60 which slides axially through a hole in the flange 2 and at the end of which a reference ring nut 61 is screwed. The latter projects beyond the lower end of the stem 60, and has a reduced diameter and an end hole, the outer (i.e. lower) flat surface of which constitutes the reference plane 62. Inside the ring nut 61, the penetrator 63 can move axially relative thereto. The penetrator 63 is fixedly secured to a tube 64 which is accommodated inside the stem 60 and extends upwardly to pass through a hole of a plate 70. In the tube 64, a lower part of the rod 52 is accommodated and its tip bears on a seat formed by a flanged stem 63' of the penetrator 63. The seat 63' is supported by the same tube 64.

The tube 64, at about the height of the pin 56, has an outer friction ring 65, with an outer spherical surface, and more above, supports an abutment ring nut 66, which by means of a spring 67 and a screw 68, secured to the column 5, pushes the tube 64 axially towards a position in which its lower conically shaped end 69 abuts against a corresponding seat provided on the ring nut 61. This causes the penetrator to project with respect to the reference plane 62.

The vertical rod 59 is integral with or fixed to the plate 70 (FIGS. 1 and 4) and the plate 70 is traversed by the columns 4 and 5. The columns pass through a hole 70' encircling the column 4 and an open fork 70' surrounding the column 5.

The comparator support 71, in the form of a tubular clamp, is mounted on said vertical rod 59 and can be tightened by screws 71', so as to be clamped in a position horizontal and perpendicular to the instrument axis. The end of a transmission comparator rod 71'' carries a follower 72 which is kept in a zero position by the block 55, when this block is kept in position by the hook 54' of the tie rod 54, so as to keep a stop ring 73 against the end of the guide 71''.

This arrangement allows to arrange the comparator C (FIG. 6) to be located outside the projected area in plan of the instrument, so that the operator can read easily the measurement, whatever is the way in which he exerts the measurement thrust with the hands.

Two plates 74 and 75 are connected to the block 55 (FIG. 3) and are directed horizontally towards the inside of the instrument. They hold between them the anti-friction ring 65. The pressure exerted by the two plates against said ring 65 is adjusted by a nut 76, on the threaded end of a pin 76', so to vary the thrust of a spring 77 disposed between the plate 75 and the nut 76.

In order to secure a contact without play between a hole of the block 55 and the pin 57 extending through it, a spring 78 is provided formed by a springy wire or plate which bears on the pin 57. Said hole, however, is enlarged so that the pin 57 presses on it at two parallel lines of contact parallel to the pin axis.

The tube 64 supports a sideways projecting pin 79 which slides in a slot 83 of the stem 60 in order to prevent it from rotating.

The instrument is used as follows.

The instrument is abutted on the surface to be tested by means of the base 1 and the measurement pressure is applied on the handles 13 and 14 or on the cover 16, as previously explained.

In order to render the thrust axial, the reference index 25 must be positioned in the centre of the transparent portion 21, which is obtained by suitably moving the cover 16 relative to the shell 6. (This is possible because of the sliding connection comprising the spherical surfaces 29 and 31 and the balls 33 interposed among them).

Under the thrust applied through the handles 13 and 14, the whole connected assembly comprising the cover 16, the cup 38 and the plate 43 slides downwardly compressing the spring 11. This sliding is followed by the sleeve 60 (FIG. 2) and the plate 70, because of the interposition of a spring 80 and of a pressure pin 81 between the stem 60 and the plate 43.

During this sliding takes place firstly the detachment of the ring nut 66 from the screw 68 and then the penetrator contacts the surface to be tested and stops. Carrying on the sliding, the reference plane 62 of the ring nut 61 will contact in turn the surface to be tested, and therefore the penetrator will have a relative backward (i.e. upward) movement and the tube 64 will slide with respect to the plates 74 and 75, overcoming the friction exerted by these plates on the ring 65, obtaining therefore the preloading of the instrument.

When the reference plane 62 abuts the surface to be tested, the assembly composed by the stem 60, the comparator C and the plate 70 stops so that the hook 54' of the tie rod 54 releases the block 55. Carrying on the sliding, the upper plug 50 contacts the end of the rod 52 so that the loading of the spring 47 transmitting to the penetrator, acts on this rod, with the simultaneous detachment of the neck 49 of the cylinder 48 from the shoulder against the cup 38 which continues its descent. In this latter phase occurs the penetration of the penetrator 63 into the material to be measured and the block 55 is free to follow exactly this movement, rotating counter-clockwise (with reference to FIG. 1) as it does so, which movement is caused by the dragging exerted by the friction ring 65 on the plates 74 and 75. The follower 72, following the movement of the block 55, transmits the displacement to be measured to the comparator C. The downward stroke of the second assembly receiving the thrust by the hands is stopped when a ring 85 (FIG. 1) in a yielding material impinges against the top of shoulder 40. In this position, the loading exceeding the necessary loading to the spring deflection is discharged through the columns 4 and 5 on the base 1.

The comparator housing 71 can be adjusted in height positioning suitably the securing screws within the respective vertically lengthened holes 84 (FIG. 2), so that the lever arm of the block 55 can be varied and hence the amplification of the penetration movement can be increased or decreased.

The tie rod 54 is connected to the flange 43 by means of a lateral bar 53 in order to give a certain resiliency to this connection which delays the release of the hook 54' with respect to the contact movement of the reference plane 62, so that probable vibrations, produced by a violent contact, do not influence the comparator, still clamped by the block 55.

The bar 53 is kept in place by two screws 86 (FIG. 2) while the spring 78, which eliminates the play between the block 55 and the pin 57, is retained by a screw 82 supported by the block 55 (FIG. 1).

During all the measurement phases the operator can keep the thrust true, in the way previously described.

SECOND EMBODIMENT

Figure 8:
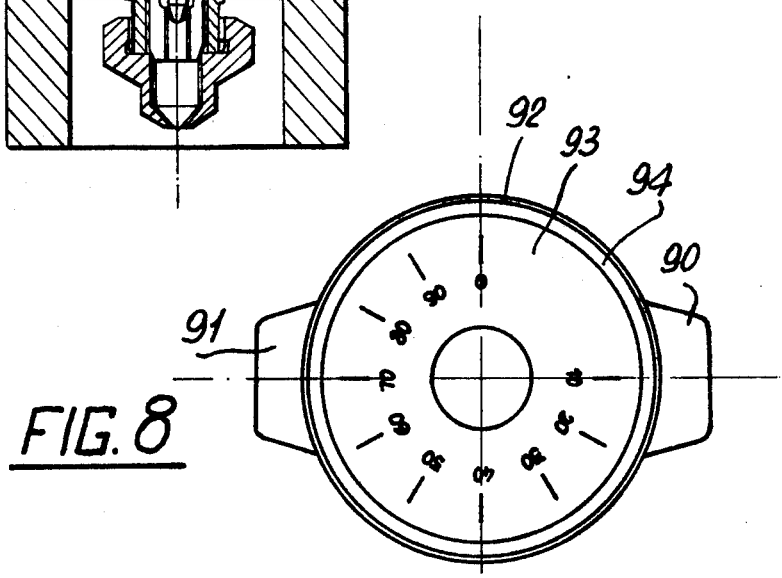
FIG. 8 is a plan view of the durometer of FIG. 7.

In the embodiment shown in FIGS. 7 and 8 the comparator is positioned at the top rather than laterally of the instrument.

With reference to FIGS. 7 and 8, the inner operating members of the durometer are not described because they are similar to those above described or of another type already known. As indicated in FIG. 7, the durometer has an outer cylindrical shell 87 mounted on and for movement relative to an inner cylindrical portion 88, carried by a base body 89 coaxially to the penetrator axis, that is, perpendicular to the surface whose hardness is to be measured.

The shell 87 has downwardly two diametrally opposed abutments or handles 90 and 91 on which a thrust is exerted with the hands and is prolonged upwardly in order to form a circular edge 92 encircling the dial 93 of the comparator. The latter may be of a type already known, for example of an hydraulic type with a spacing generating an annular gap 94.

The shell 87 takes up a position relative to the durometer axis dependent from the resultant thrust applied with the hands on the abutments 90 and 91. Consequently when said thrust is not coaxial with the axis of the instrument, and thus of the penetrator, the shell 87 has its own axis oblique and the inclination can be observed by the user because of the width change of the gap 94, so that the operator can rectify his thrust in order to take the shell 87 again to a coaxial position, which can be monitored by the width uniformity of the annular gap 94.

In order to obtain the oscillation movement of the shell 87 with respect to the inner portion 88, this latter is provided of an annular neck 95 projecting sideways and presenting the upper surface 96 preferably spherical.

In confronting relationship with the neck 95, the outer shell 87 has an inner neck 97 having a downward-facing surface 98 facing which is also spherical, the centre of curvature thereof preferably coincides with that of the surface 96.

Preferably the spherical surfaces 96 and 98 have their common centre near the abutment point of the penetrator tip on the surface of the work-piece, and this because, as tested, the trueing of the instrument can be achieved more quickly. In some cases, however, for instance when it is not possible to have an eccentricity vision, it is advisable that the common centre, whilst being always positioned on the penetrator axis, is above the abutments 90, 91 or even above the spherical surfaces 96 and 98 which then of course become concave upwardly. The surfaces 96 and 98 alternatively may be planar and normal to the axis. It is not an essential condition that the surfaces 96 and 98 are concentric; they can have different radii.

Between the surfaces 96 and 98 are interposed balls 99, in an adequate number and preferably kept on a same circumference by an annular cage 100. The use of said balls is preferable because sliding frictions are eliminated, the presence of which could provide a resistance to the shell 87, preventing it from following exactly the inclination of the thrust applied.

Such an arrangement allows the shell 87 to oscillate with respect to the inner portion 88 with a limited play only by the mutual inter-engagement which prevents the balls from breaking the contact with the surfaces 96 and 98.

Above the neck 97, an annular stop 101 is carried by the comparator, to prevent the upward detachment of the shell 87.

When the operator exerts his thrust with the hands on the projections 90 and 91 and said thrust is not exactly true with respect to the instrument axis, the outer shell 87 assumes an oblique position with respect to the inner portion 88, so that the upper edge 92, on one side, approaches the periphery of the dial 93, and on the other side, it moves away generating a width change of the gap 94, that the operator can easily survey and then rectify, operating on the handles 90 and 91 in order to take this gap again to a uniform width, positioning centrally again the portion 87, in order to take the hardness measurement.

The annular space between the cage 100 and the outer face of the inner portion 88 can be filled with a ring 102 of resilient material, such as spongy rubber. In addition, a ring 103 of spongy rubber can be provided in the space between the outer shell 87 and the comparator wall; this resilient material serving to return the cage 101 and the shell 87 towards a position more or less true and to prevent the shell oscillating freely during the instrument handling.

Of course the transmission between the hand-actuated shell 87 and the inner portion movable coaxially to transmit the force to the penetrator can be embodied in any suitable way, otherwise than by means of balls, as will be clear to one skilled in the art. For example, it can be effected by a Cardan joint with an oscillation pin or similar, depending upon the structure of the known comparator instrument employed.

I claim:

1. A hand-operable durometer constructed to be hand-pressed against a surface whose hardness is to be tested, and including a comparator upon which said hardness can be read, including a first and a second assembly, the latter at least partly surrounding the first assembly and being movable to a limited extent relative thereto, the first assembly having a facing surface positioned to be pressed against the surface whose hardness is to be tested, the second assembly including a penetrator tip movable towards the first-mentioned surface and relative to said facing surface; the durometer further including means connecting said first and second assemblies for movement laterally relative to each other and means indicating the relative lateral positions of said two assemblies, whereby the said two assemblies can take up respective positions such that in use the thrust applied to the durometer is directed substantially axially of the second assembly.

2. A durometer according to claim 1 in which the second assembly includes two laterlly-extending and diametrically-opposed handles positioned and constructed for gripping by the user when the durometer is in use.

3. A durometer according to claim 2 including a casing forming a part of the second assembly and a shell independent of the casing and forming part of the first assembly, the casing at least partly encircling the shell, being substantially coaxial with the penetrator tip, and being detachably connected to a cover which is located at the opposite end of the durometer to the penetrator tip.

4. A durometer according to claim 3 in which the comparator extends laterally outwardly from the shell to such an extent that it is outside the confines of the cover when the durometer is seen in plan.

5. A durometer according to claim 3 wherein the casing is constituted by a partly-cylindrical skirt member having an opening at one side through which said comparator extends laterally, the skirt member being connected to said cover by a rod located diametrically opposite to and in counterbalancing relationship with said comparator.

6. A durometer according to claim 5 wherein the rod and cover are connected by a bolt and an inter-engaging lug and slot device whereby the rod is rigid with the cover but can be disassembled therefrom.

7. A durometer according to claim 1 wherein the first and second assemblies have confronting spherical surfaces between which are disposed a plurality of balls located by a cage.

8. A durometer according to claim 7 wherein the said spherical surfaces have a common centre which is located on the axis of the penetrator tip.

9. A durometer according to claim 8 wherein the said common centre is located in the region of the penetrator tip.

10. A durometer according to claim 8 wherein the curvature of the surfaces is such that their common centre is on the penetrator tip axis at a point on the opposite side of said spherical surfaces from the tip.

11. A durometer according to claim 7 wherein one of said spherical surfaces has a different radius of curvature from the other.

12. A durometer according to claim 1 wherein the first and second assemblies have confronting plane surfaces both disposed substantially normal to the penetrator axis.

13. A durometer according to claim 1 wherein the indicating means is constituted by an inner circular wall of the second assembly and an outer circular wall of the first assembly which together define a generally annular gap at the end of the durometer opposite to the penetrator tip, whereby when the two assemblies are coaxial the gap appears of uniform width to the user.

14. A durometer according to claim 13 wherein the comparator is located at a central upper region of the durometer and the tip is located at a central lower region thereof.

15. A durometer according to claim 1 wherein resilient means are disposed between the assemblies urging them to their positions in which they are coaxial.

16. A durometer according to claim 1 wherein the penetrator tip is carried by a tubular member and the latter carries a frictional means, there being a pivoted block mechanism having a pair of plates in engagement with the frictional means and connected to the comparator, the construction being such that movement of the penetrator tip relative to said facing surface is transmitted via said plates and said frictional means to said comparator.

17. A durometer according to claim 16 including a bolt in co-operation with a spring means and an adjusting nut for urging the said plates towards each other whereby the engagement force between the plates and the frictional means can be varied, and play therebetween can be substantially eliminated.

18. A hand-operable durometer comprising:
 a. a first assembly
 b. a comparator carried by the first assembly for indicating a hardness reading
 c. a shell forming part of the first assembly
 d. a base connected to the shell and also forming part of the first assembly and having a facing surface to be placed on the surface to be tested, and a central hole in said facing surface
 e. a second assembly connected to the first assembly and capable of limited lateral and axial movement relative thereto
 f. means on said second assembly whereby the durometer can be pressed against the surface to be tested
 g. a penetrator tip forming part of the second assembly and movable through said hole in said base
 h. means whereby movement of said penetrator tip is transmitted to said comparator, and
 i. means including a pair of confronting surfaces separated by a plurality of balls located by a cage for effecting a connection between said first and second assemblies whereby a truly axial thrust can in use be applied to said penetrator tip by manual pressure on said second assembly.

* * * * *